United States Patent [19]

Scott

[11] Patent Number: 4,941,464

[45] Date of Patent: Jul. 17, 1990

[54] SHOULDER ARTHROSCOPY ABDUCTION APPARATUS

[76] Inventor: James W. Scott, P.O. Box 7630, Tifton, Ga. 31794

[21] Appl. No.: 377,153

[22] Filed: Jul. 10, 1989

[51] Int. Cl.⁵ ............................................. A61G 13/00
[52] U.S. Cl. .................................. 128/84 R; 128/856; 128/77; 128/87 R
[58] Field of Search ..................... 128/83, 84 R, 87 R, 128/87 C, 69, 77, 849, 846, 856

[56] References Cited

U.S. PATENT DOCUMENTS

| | | | |
|---|---|---|---|
| 2,817,333 | 12/1957 | Cole | 128/84 R |
| 3,536,072 | 10/1970 | Quello | 128/87 R |
| 3,805,774 | 4/1974 | Howard | 128/84 R |
| 3,903,878 | 9/1975 | Spann | 128/77 |
| 4,055,171 | 10/1977 | Ries | 128/87 R |
| 4,276,875 | 7/1981 | Sandegard | 128/89 R |
| 4,476,857 | 10/1984 | Levine | 128/77 |
| 4,481,942 | 11/1984 | Duncan | 128/878 |
| 4,615,339 | 10/1986 | Siwek | 128/878 |
| 4,616,637 | 10/1986 | Caspari et al. | 128/84 R |
| 4,679,552 | 7/1987 | Caspari | 128/856 |

*Primary Examiner*—Robert A. Hafer
*Assistant Examiner*—Lynda M. Cofsky
*Attorney, Agent, or Firm*—Bradford E. Kile

[57] ABSTRACT

A shoulder arthroscopy abduction apparatus for use during a diagnostic and/or surgical procedure including a generally rectangular, homogeneous forearm sleeve member having two apertures located at one end. The first aperture receives a patient's thumb and the second aperture receives a patient's little finger. The forearm sleeve member releasably attaches to a generally U-shaped gripping and support member, having a pair of lateral support arms.

15 Claims, 3 Drawing Sheets

SHOULDER ARTHROSCOPY ABDUCTION APPARATUS

BACKGROUND OF THE INVENTION

This invention relates to a novel arm abduction apparatus for use during shoulder arthroscopy. More specifically, this invention relates to a shoulder flexure and abduction device for use during an arthroscopic diagnosis and/or surgical procedure.

An arthroscope is an instrument that permits an orthopedist to visually examine the interior of a patient's joint. Initially arthroscopy was utilized by orthopedists as an examination tool to visually explore a potentially damaged knee joint. More recently the procedure has been extended to examination of other joints of the body and to use as a tool during surgery. As an example, arthroscopy has been used to diagnose and correct some of the most painful shoulder pathologies seen in orthopedic medicine.

Patients experiencing chronic shoulder complaints of pain, catching, popping, clicking, crepitus or weakness may undergo diagnostic arthroscopic surgery when physical, radiographic and/or arthrographic findings are inconclusive. The most commonly seen pathologies in such patients include glenoid labrum tears, complete or incomplete rotator cuff tears, and complete or incomplete biceps tendon tears. Other problems which can be investigated with shoulder arthroscopy are loose bodies, osteoarthritis, rheumatoid arthritis, and tumoral conditions such as synovial osteoshondromatosis.

Shoulder arthroscopy surgical procedures include the removal of loose bodies, excision of glenoid labrum tears, debridgement of rotator cuff and biceps tendon tears, debridgement and lysing of adhesions in the osteoarthritic shoulder, and synovectomy as well as abrasion arthroscopy and arthroscopy of the subdeltoid bursa.

Over the recent past, arthroscopic techniques have developed to the point that arthroscopy is one of the most common surgical procedures performed by orthopedists. During shoulder arthroscopy, the arthroscope must pass through several layers of fat and muscle and penetrate a thick capsule. Proper orientation is essential for the accurate portal placement that is necessary to avoid injury to the underlying neurovascular structures. Gaining entrance to the joint must be considered one of the most technically demanding aspects of the procedure. Consequently, the initial orientation and reliable maintenance of the operative shoulder with respect to instrumentation and the surgeon are crucial.

In shoulder arthroscopy, a patient is positioned in a lateral decubitus position with the surgical arm connected to a traction or similar device. This traction abducts and extends the arm in order to permit near-total circumferential access to the operative shoulder. A patient is moved to the posterior aspect of an operating table so that the surgeon can easily manoeuvre anterior portal instrumentation. Under usual circumstances fifteen to twenty pounds of traction is required to distract the articular surface from the humeral head of the glenoid.

In the past, traction has been achieved either manually or by securing the operative arm to a fixed point. Manual traction by an assistant is limited due to the assistant's fatigue potential and inability to hold a constant position. Moreover a logistical complication is occasioned by the cumbersomeness created by the assistant's body in close proximity to the operative area.

An option to manual traction is fixed point traction. Fixed point traction comprises tying a cord around a patient's wrist and securing the free end to a fixed point. This procedure alleviates the dependency on an assistant as a means of stabilizing the shoulder. Generally when attaching the operative arm to a fixed point, a patient's operative arm is enclosed in a protective drape comprised of a tubular knit cotton stockinette and a surrounding waterproof latex outer sleeve. A traction band is then placed about the patient's wrist overlying the outer sleeve and a traction cord is secured at the wrist by means of a slipknot and run over a pulley. This technique, although expedient, tends to induce edema in cases where constant traction was prolonged as well as post-operative discomfort in the operative wrist.

The above noted techniques were improved by wrapping the length of an operative forearm in an adhesive material and balancing the forearm over a set of pulleys thus creating a suspension system. Although the provision of a load distributing adhesive wrap and suspension system was an enhancement to fixed point traction, it is possible, particularly in the elderly, to tear skin from a patient's forearm upon removal of the adhesive. Still further, during long operative procedures, the suspension system may exhibit a degree of instability due to manipulation of the operative shoulder. Consequently, the operative forearm must be wrapped tightly to offset unwanted movement during the operative procedure. Tight wrappings, however, may constrict a patient's forearm which may lead to vascular blockage.

Modifications in forearm gripping devices have become available within the past few years which allay the difficulties experienced with the adhesive wrap. In more recent surgical procedures, a forearm engaging sheath has been envisioned. In this device, the sheath is lined with rubber and includes a pair of straps to circumferentially bind the sheath to the forearm. This engaging device, while eliminating the tourniquet characteristics of an adhesive wrap, and tendency to tear a patient's outer layer of skin upon removal does not provide an optimum degree of stability over an extended period of time.

An improvement of the above noted forearm gripping device was obtained by lining the device with a traction pad designed to extend along the length of a patient's forearm and frictionally engage the patient's forearm. Though providing the desired stability, the traction pad compresses tissue in the forearm which may limit circulation and lead to vascular blocking during extended operative procedures.

The difficulties suggested in the proceeding are not intended to be exhaustive but rather are among many which may tend to reduce the effectiveness and physician satisfaction with prior forearm gripping devices during arthroscopic diagnosis and/or surgical procedures. Other noteworthy problems may also exist; however, these presented above should be sufficient to demonstrate that shoulder arthroscopy forearm gripping devices appearing in the past will admit to worthwhile improvement.

OBJECTS AND A BRIEF SUMMARY OF THE INVENTION

Objects

It is therefore a general object of the invention to provide a novel shoulder arthroscopy abduction apparatus which will obviate of minimize difficulties of the type previously described.

It is a specific object of the invention to provide a shoulder arthroscopy abduction apparatus which may facilely flex and abduct an operative arm prior to shoulder arthroscopic diagnosis and/or surgery.

It is another object of the invention to provide a shoulder arthroscopy abduction apparatus which will eliminate the possibility of tearing an outer layer of skin from a patient's forearm upon removal of the forearm gripping device following shoulder arthroscopic surgery.

It is still another object of the invention to provide a shoulder arthroscopy abduction apparatus which will minimize the possibility of excessive compression of a patient's operative arm during surgery.

It is a further object of the invention to provide a shoulder arthroscopy abduction apparatus which will be secure in providing abducting placement of an operative arm during arthroscopic diagnosis and/or surgery.

It is yet another object of the invention to provide a shoulder arthroscopy abduction apparatus which will minimize the possibility of postoperative discomfort in a patient's wrist following surgery resulting from a constant concentrated constriction around the wrist.

It is yet still a further object of the invention to provide a shoulder arthroscopy abduction apparatus which is personalized with respect to each patient with all patient contacting portions being facile disposable following an operative procedure.

It is yet a further object of the invention to provide a shoulder arthroscopy abduction apparatus which may be easily manufactured and utilized by an orthopedic surgeon.

It is yet still another object of the invention to provide a novel sleeve operable to surround a patient's forearm during arthroscopic diagnosis and/or surgery and receive a patient's palm, thumb and little finger to promote operative cooperation with a generally U-shaped gripping and support device.

BRIEF SUMMARY OF A PREFERRED EMBODIMENT OF THE INVENTION

A preferred embodiment of the invention which is intended to accomplish at least some of the foregoing objects includes a generally rectangular, homogeneous forearm sleeve member operable to frictionally embrace a patient's forearm during shoulder arthroscopic diagnostic and/or surgical procedures. The forearm sleeve member includes a releasable retaining means for securing the sleeve member in a generally cylindrical wrap for frictionally engaging a patient's forearm.

A generally U-shaped gripping and support member is connected to an exterior surface of the wrap and includes a pair of support arms which extend longitudinally along the patient's forearm. The U-shaped member, in combination with the forearm sleeve member, forms a forearm gripping apparatus to stabilize and abduct the operative arm. The U-shaped gripping and support member is fashioned with a self-adhering strip on an interior surface of each of the pair of support arms. Each arm is operably flexed inward to releasably engage an exterior surface of the forearm sleeve wrap. The U-shaped member further includes a transverse gripping member operable to receive a patient's hand for grasping support during shoulder arthroscopy procedures.

The forearm sleeve member is generally rectangular in plan view and includes a long axis operable to lie along a patient's arm. A first end of the forearm sleeve member extends into a patient's hand and includes a pair of apertures to receive a patient's thumb and little finger. A second end of the forearm sleeve operably extends adjacent to a patient's elbow. The forearm sleeve is preferably composed of an elastomeric foam and operably envelopes a patient's forearm in a generally cylindrical wrap.

THE DRAWINGS

Other objects and advantages of the present invention will become apparent from the following detailed description of a preferred embodiment thereof taken in conjunction with the accompanying drawings, wherein.

Figure 6:
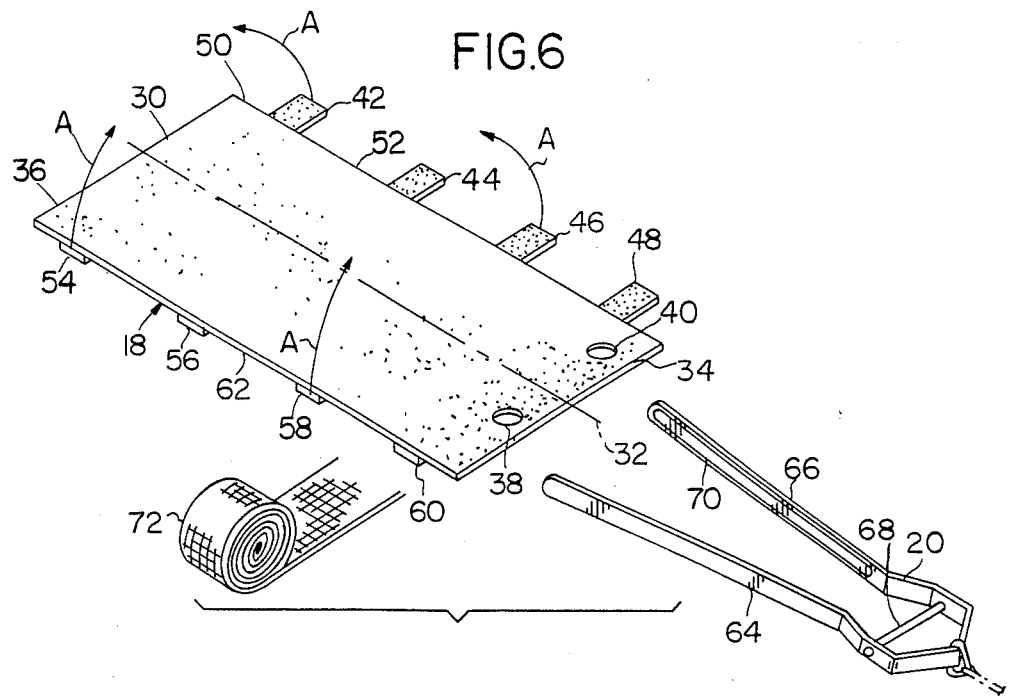
Figure 7:
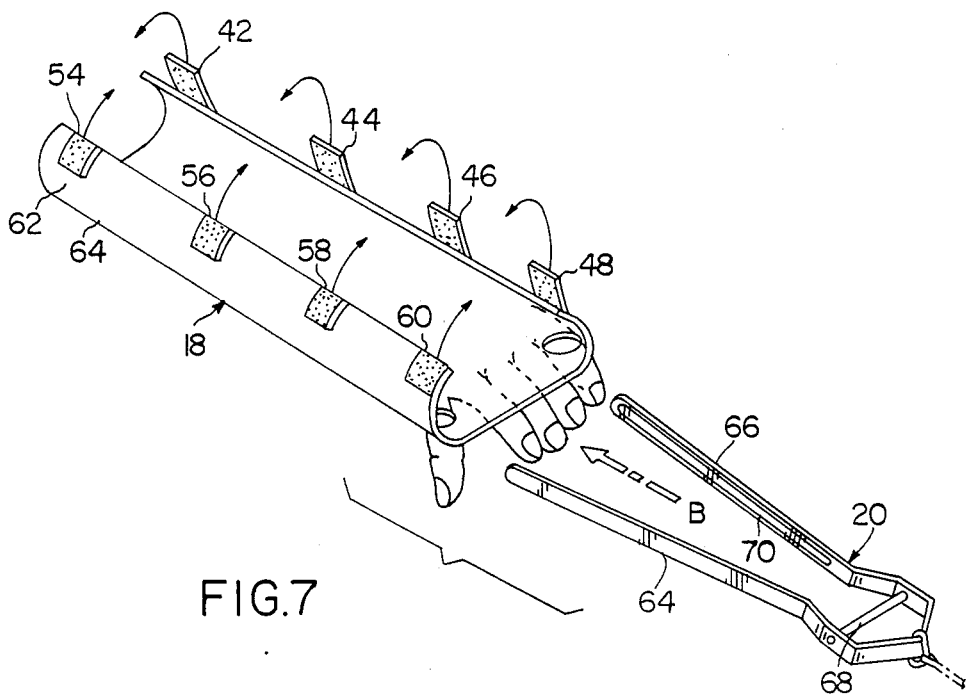

FIG. 6 is an exploded view of the subject invention including a forearm sleeve portion, a U-shaped gripping and support member, and a means for securing the sleeve portion to the support member; and FIG. 7 is a partially exploded view of the insertion of a patient's operative arm including a generally homogeneous forearm sleeve member into a generally U-shaped member in an operating theater prior to surgery.

DETAILED DESCRIPTION

Figure 1:
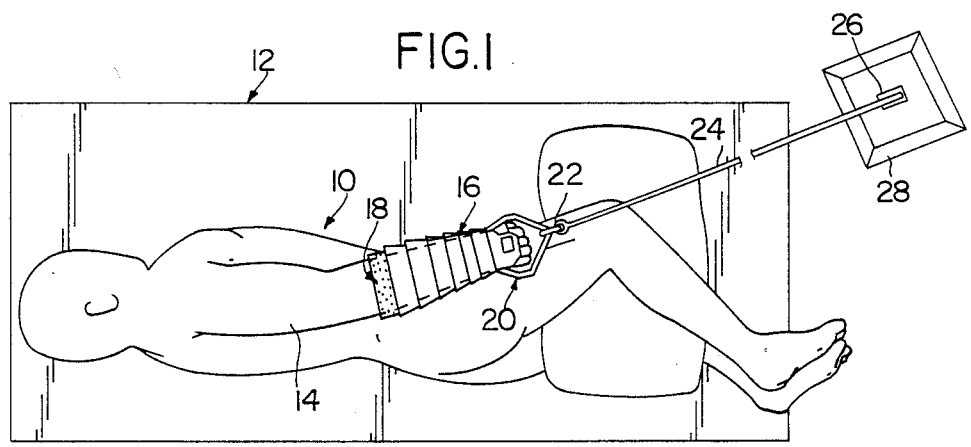
FIG. 1 is a view disclosing the context of the subject invention and depicts a patient lying upon an operating table with an operative forearm flexed and abducted by a shoulder arthroscopy abduction apparatus in accordance with a preferred embodiment of the invention.
Figure 2:
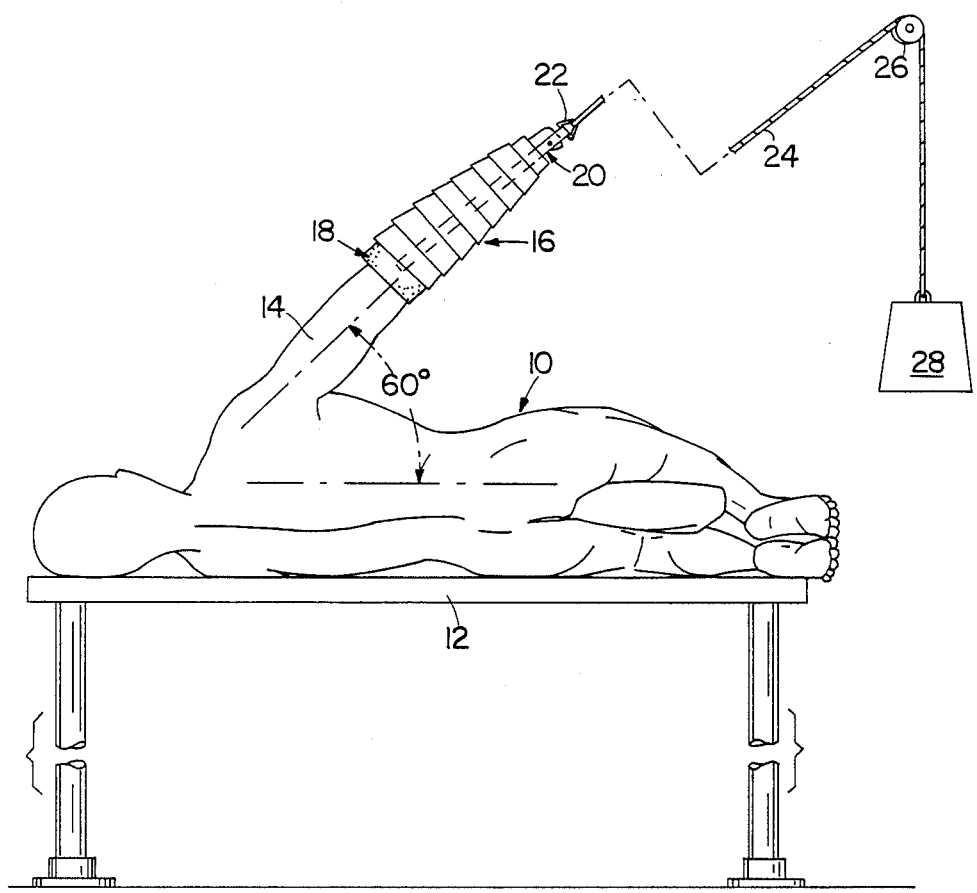
FIG. 2 is a side view of a shoulder arthroscopy abduction apparatus in accordance with the subject invention and shows a patient's arm abducted at approximately a sixty degree (60°) angle.

Referring now to the drawings, wherein like numerals indicate like parts, and initially to FIGS. 1 and 2, there will be seen an operative context of the subject invention. More particularly, a patient 10 is shown in a lateral decubitus position upon an operating table 12 with an operative arm 14 shown in a flexed and abducted posture by use of a shoulder arthroscopy abduction apparatus 16 in accordance with a preferred embodiment of the subject invention.

The shoulder arthroscopy abduction apparatus 16 includes a generally homogeneous forearm sleeve member 18 which releasably enrobes the forearm of a patient 10 and a U-shaped gripping and support member 20. The U-shaped gripping and support member 20 is attached, as at position 22, to a cable 24 which in turn is trained over a pulley 26 and connected to a weight 28 placing the patient's arm in traction. This weight may be from ten to twenty pounds depending upon the arthroscopic procedure contemplated.

FIG. 2 is a side view of the patient disclosed in FIG. 1. By utilization of the subject shoulder arthroscopy abduction apparatus 16, it will be noted that the patient's arm may be elevated, flexed and abducted approximately sixty (60°) degrees or so and maintained in a secure position during an arthroscopy procedure.

Turning now to FIGS. 3–7, there will be seen various detailed views of a shoulder arthroscopy abduction apparatus 16 in accordance with a preferred embodiment of the invention. The subject apparatus 16 includes a generally homogeneous forearm sleeve member 18 and a generally U-shaped gripping and support member 20.

Referring specifically to FIG. 6, note sheet 3, the homogeneous forearm sleeve member 18 includes a generally rectangular arm engaging pad 30. This pad 30 is composed of an elastomeric foam composition and has a long central axis 32 operable to lie along a patient's arm. The pad 30 is flexible and elastically wraps around a patient's forearm, note directional arrows A, to securely embrace the forearm. The pad 30 has a first end 34 operable to extend to a patent's hand and a second end 36 extending to a patient's elbow. A first 38 and second 40 aperture are fashioned through the first end 34 of the pad 30. The first aperture 38 receives a patient's thumb, and the second aperture 40 receives a patient's little finger. The first end of the pad 30 therefore lies within the patient's palm.

As noted above, the pad 30 is designed to elastically wrap around a patient's forearm and a set of fastening straps 42, 44, 46, and 48 are axially spaced along one lateral edge 50 of an exterior surface 52 of the engaging pad 30. A set of retaining patches 54, 56, 58, and 60 are mounted upon an opposing edge 62 of the pad and are axially spaced to correspond with fastening straps 42–48.

Referring particularly to FIG. 7, the retaining patches 54, 56, 58 and 60 releasably engage the fastening straps 42, 44, 46, and 48 to form the generally rectangular pad 30 into a cylindrical wrap 64 about a patient's forearm.

The straps and pads may be composed of conventional fastening assemblies but in a preferred embodiment comprise hook and loop type releasable retaining members of the VELCRO type. The composition of the pad 30 may be composed of a variety of materials but preferably is composed of a natural or synthetic foam rubber composition, polyurethane foam, or the like, which exhibits an elastic or resilient property and thus is operable to circumferentially grip a patient's forearm in a manner to distribute normal forces all along the forearm and provide an extended area of frictional engagement with the patient's arm.

The outer surface of the pad 30 is covered with a loop type cloth material 62 which is operable to engage with and releasably receive hook like members of a Velcro type fastening strip.

The U-shaped gripping and support member 18 comprises a pair of support arms 64 and 66 which extend axially along a patient's forearm and a bulbous connecting segment. A transverse gripping member 68 spans the U-shaped gripping and support member 18 to receive a patient's hand for grasping support. A patient's wrist is thus held in an upright posture so that a concentrated strain is not placed on the wrist area during an operative procedure.

The apertures 38 and 40 allow the forearm sleeve member 30 to extend across a patient's palm and ensure that contact between the transverse gripping member 68 and a patient's hand is cushioned.

It will be noted by reference to FIGS. 6 and 7 that the arms 64 and 66 of the U-shaped gripping and support member 20 are inclined outwardly in a relaxed state. Accordingly, a patient's arm, wearing the sleeve member 18, may be axially extended into the U-shaped member in the direction of arrow B and the arms 64 and 66 having hook type fastening strips 70 mounted upon an inner surface of the arms may be flexed into engagement with opposed lateral surfaces of the forearm sleeve member 18.

Figure 3:
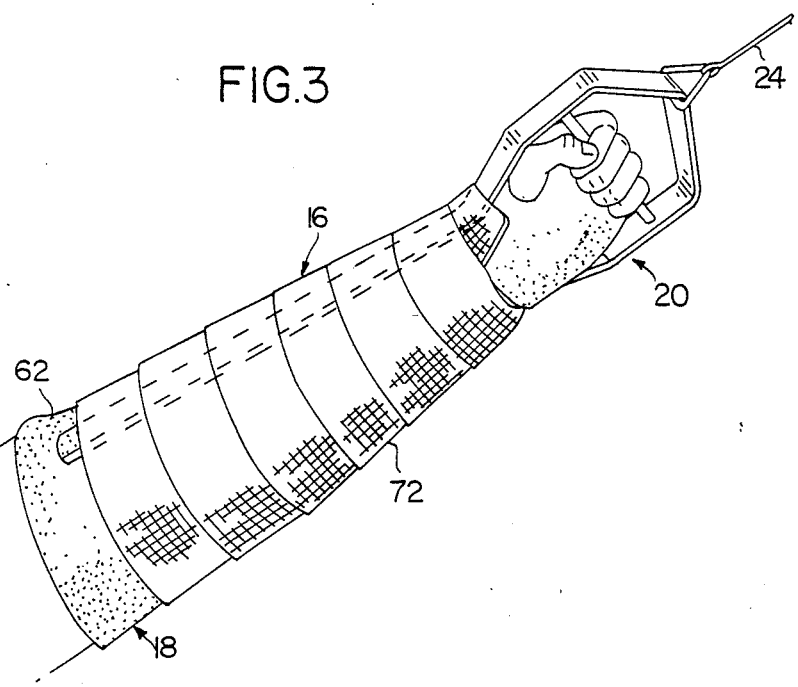
FIG. 3 is an axonometric detail view of the subject invention including a generally homogeneous forearm sleeve member and a U-shaped gripping and support member externally secured to the sleeve place by a outer wrap.
Figure 4:
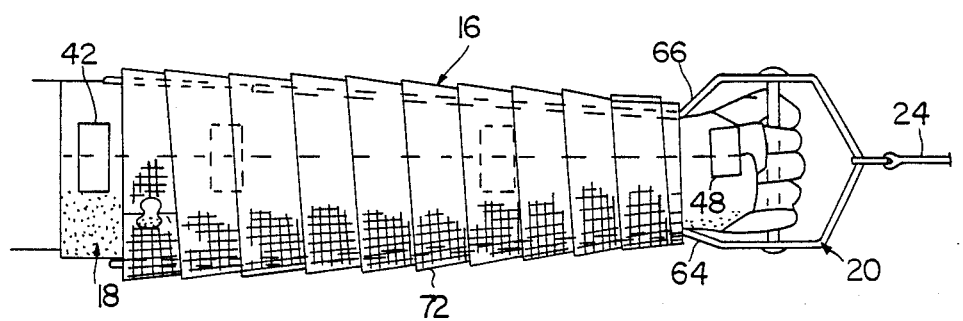
FIG. 4 is a top view of the subject invention including a releasable retaining means located on the forearm sleeve portion for facilely securing the sleeve portion in a cylindrical wrap.
Figure 5:
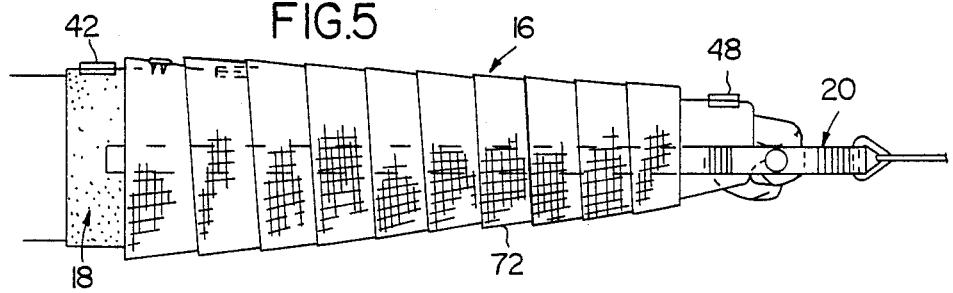
FIG. 5 is a side view of the subject invention, disclosed in FIG. 4, including a U-shaped gripping and support member operable to longitudinally attach along the forearm sleeve portion.

In order to enhance binding contact of the hook type strips 70 with the loop type cloth covering 62 of the sleeve member, an elastic wrap 72 may be operably wound around the apparatus as shown in FIGS. 3–5. This elastic wrap 72 has the synergistic advantage of supplementing and enhancing an even distribution of compressive forces along the patient's forearm.

SUMMARY OF MAJOR ADVANTAGES OF THE INVENTION

After reading and understanding the foregoing description of the subject shoulder arthroscopy abduction apparatus, in conjunction with the drawings, it will be appreciated that several distinct advantages of the subject invention are obtained.

Without attempting to set forth all of the desirable features of the instant shoulder arthroscopy abduction apparatus, at least some of the major advantages of the invention includes the combination of a separate forearm sleeve member 18 and a U-shaped gripping and support member 20. The forearm sleeve member may be applied to a patient's operative arm in the patient's room and worn to the operating theater. The U-shaped gripping and support member 20 may remain in the operating room and in Attachment to a table traction stand and laterally, and facilely, applied to a patient's operating arm prior to surgery.

Since the subject shoulder arthroscopy abduction apparatus has been composed of two major elements, the patient contacting forearm sleeve member is disposable and the patient is specific while the U-shaped gripping and support member 20 may remain in the operating theater and may be repetitively used just as the other elements of the traction equipment can be used with a number of patients.

The elastomeric homogeneous forearm sleeve member 18 embraces a patient's forearm and does not rely on a concentrated constriction or adhesive binding to a patient's skin to be maintained in position. Rather frictional engagement along the patient's entire forearm, coupled with a lateral elastomeric compressive force is suitable to provide a secure forearm attachment. This compressive gripping arrangement is enhanced by the provision of the exterior elastomeric wrap 72 which synergistically binds the arms 64 and 66 of the U-shaped gripping and support member 20 to the sleeve member 18.

The generally homogeneous forearm sleeve member 18 is covered with a loop-type like cloth operable to receive a releasably retaining hook-type fastening member or strips mounted upon the interior surfaces of the arms 64 and 66 of the U-shaped gripping and support member. Accordingly, a physician can adjust the abduction apparatus in the operating theater as needed.

The generally homogeneous forearm sleeve member 18 includes a pair of apertures 38 and 40 at a first end thereof and receives a patient's thumb and little finger to enable a first end of the generally cylindrical sleeve to extend across the palm of a patient's hand. This resilient buffer is operably placed against a transverse gripping member 68 of the U-shaped gripping and support member 20 and enables a physician to operably position the U-shaped member in a secure retaining posture and support a patient's wrist without tension during arthroscopy surgery.

In describing the invention, reference has been made to a preferred embodiment and illustrative advantages of the invention. Those skilled in the art, however, and familiar with the instant disclosure of the subject invention, may recognize additions, deletions, modifications, substitutes and then other changes which will fall within the purview of the subject invention and claims.

What is claimed is:

1. A shoulder arthroscopy abduction apparatus for use during a diagnostic and/or surgical procedure comprising:
   a generally rectangular, forearm sleeve member having,
      a long axis operable to lie along a patient's arm and flexibly yet securely embrace a patient's forearm, and
      at least one releasable retaining means for securing said generally rectangular forearm sleeve member in a generally cylindrical wrap about a patient's forearm;
   a generally U-shaped gripping and support member having,
      a transverse gripping member operable to receive a patient's hand for grasping support, and
      a pair of support arms operable to extend along opposing lateral portions of a patient's forearm; and
   means connected between an inside surface of said pair of support arms of said generally U-shaped gripping and support member and an external surface of said generally rectangular forearm sleeve member for releasably attaching said generally U-shaped gripping and support member to said generally rectangular forearm sleeve member.

2. A shoulder arthroscopy abduction apparatus as defined in claim 1 wherein:
   said generally rectangular, forearm sleeve portion is composed of a generally homogeneous elastomeric foam.

3. A shoulder arthroscopy abduction apparatus as defined in claim 1 wherein said generally rectangular forearm sleeve member comprises:
   a first end operable to extend into a patient's hand;
   a second end operable to extend adjacent to a patient's elbow; and
   a first and second aperture fashioned through said first end of said forearm sleeve member for receiving a thumb and little finger of a patient and facilitating grasping of said transverse gripping member of said generally U-shaped gripping and support member by a patient.

4. A shoulder arthroscopy abduction apparatus as defined in claim 1 wherein said at least one releasable retaining means comprises:

at least one fastening strap connected to a lateral wall surface of said generally rectangular forearm sleeve portion; and
   at least one retaining patch connected to an opposed lateral wall surface of said generally rectangular forearm sleeve member and said fastening strap operably forming said generally rectangular, forearm sleeve member into a generally cylindrical wrap around a patient's forearm.

5. A shoulder arthroscopy abduction apparatus as defined in claim 4 wherein said at least one releasable retaining means comprises:
   at least two independent fastening straps axially spaced along said lateral wall surface of said forearm sleeve member; and
   at least two independent retaining patches axially spaced along an opposed lateral wall of said forearm sleeve member and opposite said fastening straps and being operable to releasably attach to said fastening straps.

6. A shoulder arthroscopy abduction apparatus as defined in claim 1 wherein:
   said generally U-shaped gripping and support member is composed of a flexible, aluminum alloy.

7. A shoulder arthroscopy abduction apparatus as defined in claim 1 wherein each of said pair of support arms of said generally U-shaped gripping and support member includes:
   an attachment strip positioned on an interior surface of each of said pair of support arms to releasably attach to an exterior surface of said forearm sleeve member.

8. A shoulder arthroscopy abduction apparatus as defined in claim 7 wherein:
   said attachment strip is composed of a hook type fastening material operable to releasably attach to said forearm sleeve member.

9. A shoulder arthroscopy abduction apparatus as defined in claim 1 wherein:
   each of said pair of support arms angle, in a relaxed state, outwardly and may be flexed inward, following axial positioning, to releasably engage and attach to opposed lateral surfaces of said forearm sleeve member.

10. A shoulder arthroscopy abduction apparatus for use during a diagnostic and/or surgical procedure comprising:
   a generally rectangular, forearm sleeve member having,
      a long axis operable to lie along a patient's arm and flexibly yet securely embrace the homogeneous a patient's forearm,
      a first end operable to extend into a patient's hand,
      a second end operable to extend adjacent to a patient's elbow, and
      a first and second aperture fashioned through said first end of said homogeneous forearm sleeve member for receiving a thumb and little finger of a patient;
   at least one fastening strap connected to a lateral surface of said generally rectangular, forearm sleeve member;
   at least one retaining patch connected to a an opposed lateral surface of said forearm sleeve member and cooperating with said fastening strap to operably form said generally rectangular, forearm sleeve member into a generally cylindrical wrap around a patient's forearm;

a generally U-shaped gripping and support member having,
- a transverse gripping member operable to receive a patient's hand for grasping support, and
- a pair of support arms operable to extend along opposing lateral portions of a patient's forearm; and means connected between an inside surface of each of said pair of support arms of said generally U-shaped gripping and support member and an external surface of said generally rectangular, homogeneous sleeve member for releasably attaching said generally U-shaped gripping and support member to said generally rectangular forearm sleeve member.

11. A shoulder arthroscopy abduction apparatus as defined in claim 10 wherein said transverse gripping member comprises:
- a cylindrical rod positioned so as to span the junction of said pair of support arms to permit grasping by a patient and to assist in maintaining an axial position of said U-shaped gripping and support member.

12. A shoulder arthroscopy abduction apparatus as defined in claim 11 wherein said at least one fastening strap comprises:
- at least two independent fastening straps axially spaced along said lateral surface of said forearm sleeve member.

13. A shoulder arthroscopy abduction apparatus as defined in claim 12 wherein at least one retaining patch comprises:
- at least two independent retaining patches axially spaced along an opposed lateral surface of said forearm sleeve member and opposite to said fastening straps and being operable to be releasably attached to said fastening straps.

14. A shoulder arthroscopy abduction apparatus as defined in claim 13 wherein:
- each of said pair of support arms is angled, in a relaxed state, outwardly and may be flexed inwardly, following axial positioning, to releasably engage and attach to an exterior surface of said forearm sleeve member.

15. A shoulder arthroscopy abduction apparatus as defined in claim 14 wherein:
- said generally U-shaped gripping and support member is composed of a flexible aluminum allow material.

* * * * *